United States Patent [19]

Krezanoski

[11] 4,046,706
[45] Sept. 6, 1977

[54] CONTACT LENS CLEANING COMPOSITION

[75] Inventor: Joseph Zenon Krezanoski, Los Altos, Calif.

[73] Assignee: Flow Pharmaceuticals, Inc., Palo Alto, Calif.

[21] Appl. No.: 674,159

[22] Filed: Apr. 6, 1976

[51] Int. Cl.$^2$ .......................... C11D 1/94; C11D 1/88
[52] U.S. Cl. ......................................... 252/106; 134/2; 134/40; 134/42; 252/542; 252/DIG. 7
[58] Field of Search ................ 252/542, 106, DIG. 7; 134/40, 42, 2; 424/78, 269

[56] References Cited

U.S. PATENT DOCUMENTS

| | | | |
|---|---|---|---|
| 2,773,068 | 12/1956 | Mannheimer | 252/542 X |
| 2,781,356 | 2/1957 | Mannheimer | 252/542 X |
| 3,882,036 | 5/1975 | Krezanoski et al. | 252/106 |
| 3,884,826 | 5/1975 | Phares et al. | 252/106 |
| 3,888,782 | 6/1975 | Bognosian et al. | 252/542 X |
| 3,925,241 | 12/1975 | Schmolka | 252/542 X |
| 3,954,644 | 5/1976 | Krezanoski | 252/106 |
| 3,969,281 | 7/1976 | Sharp | 252/542 |

OTHER PUBLICATIONS

Hackh's Chemical Dictionary, 4th Ed., McGraw Hill Book Co., New York, 1969, p. 249.

*Primary Examiner*—Harris A. Pitlick
*Attorney, Agent, or Firm*—Finnegan, Henderson, Farabow & Garrett

[57] ABSTRACT

A composition for cleaning contact lenses is provided. The composition comprises a poly(oxyethylene)-poly(oxypropylene) block copolymer having a molecular weight between about 1900 and 15,500, a water solubility in excess of about 10 gms per 100 ml, a cloud point in 1% aqueous solutions above about 30° C, and a foam height in excess of 30 mm; a microbial growth inhibitor; ethyl or isopropyl alcohol; an amphoteric surfactant; and water.

19 Claims, No Drawings

CONTACT LENS CLEANING COMPOSITION

FIELD OF INVENTION

The present invention relates to various contact lens cleaning compositions, and more particularly to aqueous compositions containing a poly(oxyethylene)-poly(oxypropylene) block copolymer, a germicidal composition to preserve the sterility of the solution, isopropyl alcohol, and an amphoteric surfactant. Depending upon the particular formulation, the compositions of the present invention may be used to clean soft contact lenses, such as flexible silicone contact lenses and polyhydroxylated alkyl methacrylate contact lenses, cellulose acetate butyrate contact lenses, and conventional hard polymethacrylate lenses. The cleaning compositions are particularly suitable for removing cholesterol like materials, and ocular debris, which can be removed from lenses only with great difficulty and which are not adequately removed by conventional contact lens cleaning compositions.

BACKGROUND OF THE INVENTION

The proper care of contact lenses can be viewed as requiring three necessary steps. First, after removal from the eye the lenses must be cleaned to physically remove foreign matter from their surfaces. Second, the lenses must be disinfected. Finally, the lenses must be prepared for insertion into the eye.

In the past, contact lenses have been made of hard polymethacrylates. Proper care of these lenses has required that they be stored in specially developed cleaning and storage solutions to maintain them in good order when not in use. The storage solutions are formulated to disinfect the lenses during the lenses' storage. Many of these cleaning and storage solutions contain chlorobutanol as a preservative which acts to preserve the sterility of the solution.

Recently, a new type of contact lens known as a soft lens has been developed. Soft lenses can be divided into two broad categories, namely hydrophilic lenses and hydrophobic lenses. The care of each of these lenses presents special and different problems.

Hydrophobic contact lenses are usually based on elastic and flexible silicone rubber (polysiloxane), and are generally made from cross-linked dimethyl polysiloxane which is commonly known as Antifoam A. A typical preparation of a hydrophobic silicone contact lens is disclosed in U.S. Pat. No. 3,228,741. Clinical testing of flexible silicone rubber lenses has created a need for cleaning compositions that can be effectively used with these lenses.

In testing the commercially available compositions designed for conventional hard polymethylmethacrylate contact lenses, it has been found that they are not adequate and in some instances detrimental to the successful use of flexible silicone contact lenses. For example, it has been found that the preservative chlorobutanol, present in many commercially available solutions designed for hard polymethylmethacrylate lenses, is adsorbed and concentrated by silicone lenses. This ability of the silicone elastomer to concentrate chlorobutanol could ultimately change the physical and chemical properties of the lenses to make them ineffective in providing visual correction.

Moreover, patients experimentally wearing flexible silicone rubber lenses stored in a chlorobutanol containing storage solution have complained of discomfort. This was found to be directly associated with the high concentrations of chlorobutanol in the silicone lenses thus treated.

The highly hydrophobic nature of the silicone elastomer has prevented their uniform and effective cleaning and wetting by all available conventional cleaners and wetting agents. Thus, various generic classes of organic compounds have been screened including alcohol with varying degrees of acetylation, polysaccharides, lanolin derived nonionic surfactants, ethoxylated sorbitol anhydrides, and vaious cationic, anionic and nonionic detergents, but to date none have been found acceptable.

Hydrophilic soft contact lenses are hydrated gel lenses which can be prepared by copolymerizing hydrophilic organic monomers having an olefinic double bond with a small amount of a cross-linking agent usually having two polymerizable, olefinic double bonds. These lenses are usually based on polyhydroxylated alkyl methacrylates, such as polyhydroxyethyl methacrylate, cross-linked with, for example, a hydroxyethyl dimethacrylate. Usually, there is about one (1) cross-linking molecule for every 200 monomer units. By comparison, the conventional hard contact lens consists of polymethylmethacrylate cross-linked with hydroxyethyl dimethacrylate. The absence of a hydrophilic OH group in conventional hard lenses accounts for the tremendous difference in behavior of the two materials.

Hydrated gel lenses can contain the following materials: (1) hydroxyethylmethacrylate (HEMA) or its analogues, (2) ethylene-glycol dimethacrylate (EGMA) or its analogues, (3) polymethylmethacrylate (PMMA) or its analogues, (4) polyvinylpyrrolidone (PVP), (5) traces of the respective monomers, (6) traces of inhibitors such as hydroquinine, (7) traces of catalysts such as benzoyl peroxide, and (8) water. A more detailed description of hydrated gel lenses is found in U.S. Pat. Nos. 2,976,576; 3,220,960; 3,361,858; 3,408,429; 3,496,254; and 3,499,862.

Soft contact lenses of the hydrated gel type have a number of properties which complicate their effective care. For example, the hydrophilic OH groups of the lenses attract and hold large amounts of water in the plastic, and this leads to difficulties in cleaning and sterilizing the lenses. Further difficulties in caring for hydrated gel lenses occur because these lenses complex and concentrate chlorobutanol, benzalkonium chloride, thimerosal, phenylmercuric nitrate and other preservatives found in solutions for conventional lenses. Generally, these preservatives are inactivated in the complexed state. Also, if concentrated preservatives are released too rapidly at the cornea, they may cause chemical burns. Thus, solutions and cleaners now available for conventional hard lenses cannot be used with gel lenses.

Another type of contact lens which has recently been developed is the semi-rigid, gas permeable, cellulose acetate butyrate lens. These lenses are somewhat more flexible than conventional hard polymethacrylate lenses, but less flexible than the common soft lenses.

Cellulose acetate butyrate lenses are based on organic cellulose esters produced by the reaction between chemical cellulose and the appropriate acid and anhydrides in the presence of a suitable chemical catalyst. For example, cellulose acetate, prepared by treating cotton linters with sulfuric acid and acetic acid, may be esterified with a mixture of butyric acid, acetic anhydride, and a small amount of a concentrated sulfuric acid catalyst. The reaction is allowed to proceed virtually to completion, so that the cellulose fiber structure completely disappears to produce a uniform, homogeneous product. A typical preparation of a cellulose acetate butyrate contact lens is disclosed in U.S. Pat. No. 3,900,250.

Cellulose acetate butyrate lenses have a number of advantages. Because of their flexibility, they are less irritating upon contact with the eye during the initial stages of adaptation by the wearer and during permanent wearing. Furthermore, while the lens material is flexible to the extent it is practically unbreakable in normal use, it has sufficient rigidity to be easily machined. However, care of these lenses is complicated by the fact that, like hydrated gel type lenses, they tend to complex and concentrate certain preservatives, such as benzalkonium chloride, commonly used in solutions for conventional hard lenses.

The methods currently used in caring for hydrophilic gel lenses generally include the following: (1) boiling in saline; (2) treating with 3% hydrogen peroxide; (3) rinsing with "sterile" saline; and (4) storing in disinfecting solutions. Each of these methods, however, have numerous disadvantages.

For example, boiling in saline kills pathogens but does not kill spores. Another disadvantage of boiling is that it is not convenient for patients to carry the boiling devices with them wherever they go. Further, proteins and other materials may be denatured and deposited on or in the lens matrix if the lenses are not adequately cleaned prior to boiling. The effects of boiling on soluble or water dispersible proteins are similar to the coagulating and insolubilizing effects of heat on egg whites. Thus, once these deposits are allowed to accumulate on the lenses, substantially more effort is required to clean them.

Commercial hydrogen peroxide has satisfactory germicidal activity, but its use also has a number of disadvantages. Commercial hydrogen peroxide has a pH of about 3 and it is therefore necessary to treat the lenses with sodium bicarbonate solution to neutralize the high acidity before the lenses can be worn safely. A major concern, however, is the ever present possibility that the patient will forget to neutralize and dilute the hydrogen peroxide with sodium bicarbonate solution prior to inserting the lens. further, the cleaning action of hydrogen peroxide is no better than that achieved with water or isotonic salt solutions. In fact, hydrogen peroxide, because of its oxidative chemical reactivity, can denature and precipitate proteins.

Rinsing lenses with unpreserved and supposed "sterile" saline solution delivered from a large multiple dose bottle, is far from adequate in sterilizing lenses.

Experimental isotonic disinfecting solutions of two basic types are currently available. One solution contains 0.001% thimerosal, 0.1% disodium ethylenediaminetetraacetate, and 0.005% chlorhexidine gluconate. Another solution has the same composition except that the chlorhexidine gluconate is replaced with a like amount of dodecyl triethanolamine hydrochloride. Both of these solutions have drawbacks.

Chlorhexidine and dodecyl triethanolamine are not only inactivated by many peptides, proteins and fatty substances of natural origin bearing a net negative charge, but cause the formation of insoluble precipitates. To a lesser extent, this same phenomenon may occur when the negatively charged thimerosal ion reacts with proteins bearing a net positive charge. Further, neither solution is ideal when prolonged wearing comfort, complete sterility reliance and lack of allergic response are considered. Although these solutions have been tested for their cleaning efficiency, they fall significantly short of accomplishing this objective when used on a routine basis. This is not surprising since neither of these solutions was specifically formulated for this purpose.

U.S. Pat. No. 3,882,036, issued May 6, 1975 and U.S. Pat. application Ser. No. 377,430, filed July 9, 1973, now U.S. Pat. No. 3,954,644, disclose compositions suitable for cleaning hard and soft contact lenses. The compositions therein disclosed, particularly those containing poly(oxypropylene)-poly(oxyethylene) block copolymers, have proven to be very effective for cleaning flexible silicone lenses.

The disclosed cleaning compositions, however, are not as effective as would be desired with respect to removal from lenses, particularly cellulose acetate butyrate and soft lenses, of cholesterol like materials. If such material is not thoroughly removed, it may build up on or in the lenses, imparing their optical clarity and thus their usefulness. Furthermore, a build up of such materials can affect the wetability of the lenses, thus decreasing wearer comfort.

In addition, cholesterol like material remaining in or on the lenses may eventually inactivate even the best germicidal agents, and serve as a growth medium for a variety of microorganisms. While many germicidal chemicals, in appropriate concentrations, are effective in disinfecting new lenses, the same chemicals do not necessarily disinfect a lens which has been worn repeatedly and improperly cleaned.

The necessity for proper cleaning of all types of contact lenses, particularly soft silicone or hydrophilic gel lenses, is readily apparent. Single compositions suitable for use with any type of contact lenses clearly would be desirable and no compositions heretofor available are totally suitable for routine cleaning of soft lenses.

SUMMARY OF INVENTION

The present invention pertains to aqueous compositions for cleaning contact lenses which comprise:
a. about 0.01% to about 40% of a poly(oxyethylene)-poly(oxyproplyene) block copolymer having a molecular weight between about 1900 and 15,500, a water solubility in excess of about 10 gms/100 ml, a cloud point in 1% aqueous solution above about 30° C and a Foam Height in excess of 30mm;
b. a sufficient amount of a germicidal composition compatible with the lenses to preserve the sterility of the composition;
c. about 2% to about 25% ethyl or isopropyl alcohol; and
d. about 2% to about 25% of an amphoteric imidazole surfactant having the formula

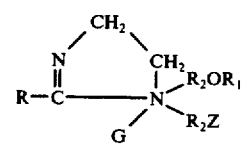

in which R is a $C_6$ to $C_{24}$ hydrocarbon radical, such as a straight or branch chain, saturated or unsaturated, aliphatic hydrocarbon or an alkyl-aryl group in which the alkyl group contains at least six carbon atoms, and preferably a fatty acid radical; $R_1$ is H, alkali metal, preferably Na, or $CH_2COOM$; the $R_2$ groups, which may be the same or different are $C_1$ to $C_4$ alkylene groups, such as $-CH_2-$, $-C_2H_4-$, $-C_3H_6-$ or $-C_4H_8-$ Z is

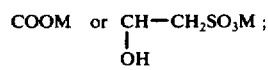

M is alkali metal, preferably Na, H, or a nitrogen containing organic base radical; and G is OH, the salt of a $C_6$ to $C_{24}$ anionic surface active sulfate or sulfonate, such as a saturated or unsaturated aliphatic sulphate or sulfonate, or an alkyl-aryl sulfate or sulfonate in which the alkyl group contains at least 6 carbon atoms, or an acid salt.

The remainder of the composition may comprise solely water or may include various other ingredients which will impart special properties. For example, various alkaline metal and alkaline earth metal salts may be added to the composition to adjust the osmotic properties (tonicities) of the compositions to make them better tolerated by living tissue. Specifically, the composition may additionally include a sufficient amount of water soluble salt compatible with ocular tissue to provide a solution salt content equivalent to about 0.5% to about 1.8% sodium chloride. Other ingredients which do not detrimentally affect the cleaning compositions of course also may be included.

DESCRIPTION OF PREFERRED EMBODIMENTS

The aqueous contact lens cleaning compositions of the present invention contain a physiologically-acceptable and chemically compatible poly(oxyethylene)-poly(oxypropylene) block copolymer. Suitable block copolymers are those sold under the trademark "PLURONIC" by Wyandotte Chemical Corp.

The products sold under the trademark "PLURONIC" are a series of closely related block polymers that may be generically classified as polyoxypropylene-polyoxyethylene condensates terminating in primary hydroxyl groups. They are formed by the condensation of propylene oxide onto a propylene glycol nucleus followed by the condensation of ethylene oxide onto both ends of the polyoxypropylene base. The polyoxyethylene hydrophilic groups on the ends of the molecule are controlled in length to constitute anywhere from 10% to 80% by weight of the final molecule. This series of products may be represented empirically by the formula:

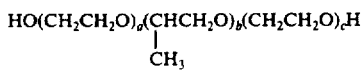

where $a$ and $c$ are statistically equal. These polyol block copolymers are nonionic surface-active agents.

In accordance with the invention, certain members of this series of block polymers having a particular combination of physical and chemical properties have been found to be effective cleaning agents for conact lenses. Thus, the polyoxypropylene-polyoxyethylene block copolymers useful in the present invention have a molecular weight between about 1900 and 15,500, and a water solubility in excess of about 10 gm/100 ml.

Additionally, the block copolymers useful in the present invention must have a cloud point in 1% aqueous solution above about 30° C, and a Foam Height in excess of 30 mm. The cloud point is the temperature at which a waxy solid material appears in solution as a 1% aqueous solution of the block copolymer is cooled. The Foam Height is the value obtained on a Dynamic Foam Tester operated at a temperature of 120° F using a 0.1% polyol concentration at a flow rate of 400 ml/min for ten minutes.

An additional requirement of the block copolymers used in the lens treating compositions of the present invention is that they be physiologically-acceptable so that no adverse reaction occurs when the solution comes in contact with human tissue or fluids. Thus, aqueous solutions of the block copolymers must be inert when they are tested for ocular tolerance in human and rabbit eyes.

Among the polyoxypropylene-polyoxyethylene block copolymers satisfying the above conditions are the following PLURONIC copolymers: Pluronic F-68, Pluronic L-44, Pluronic L-62, Pluronic L-64, Pluronic F-108, and Pluronic F-127. Pluronics F-68, L-44, L-62, L-64, F-108 and F-127 when tested in concentrations of 10%-25% show only minimal or no eye irritation. The following Table I lists the properties of a number of the block copolymers that can be used in the present invention.

TABLE I

| PLURONIC | Average Molecular Weight | Cloud Point in 1% Aq. Solution, °C | Solubility in Water | FOAMING PROPERTIES Foam Height (mm) at flow of 400 ml/mm |
|---|---|---|---|---|
| 1) L44 | 2200 | 65 | 10 | 360 |
| 2) L62 | 2500 | 32 | 10 | 35 |
| 3) L64 | 2900 | 58 | 10 | 600 |
| 4) F68 | 8350 | 100 | 10 | 600 |
| 5) F108 | 15500 | 100 | 10 | 425 |
| 6) F127 | 11500 | 100 | 10 | 250 |

The cleaning compositions of the present invention contain from about 0.01% to about 40% of the block copolymer, and preferably contain about 10% to about 25%, e.g., about 15%, of the block copolymer. A particularly preferred block copolymer is sold under the trademark "PLURONIC F-127".

The block copolymers are effective to remove proteins, fats, and mucopolysaccharides that accumulate on lens surfaces when they come in contact with ocular tissues and fluids. The block copolymers also act to help maintain the germicidal storage container in a generally clean state.

The contact lens cleaning compositions of the present invention also include a sufficient amount of a germicidal composition compatible with the lenses to preserve the sterility of the composition. The inclusion of a germicide is particularly important where multidose bottles of the composition are prepared. A germicide prevents bacteria from contaminating the composition after its container has been opened an initial use has been made of a portion of the solution.

Any of the well-known germicidal agents which are comparible with the particular type of contact lens to be cleaned by the composition may be employed. Specific examples of suitable preservative agents include thimerosal sodium, cetylpyridinium chloride, benzalkonium chloride, benzethonium chloride, sorbic acid, phenylmercuric nitrate, chlorhexidine, sodium salts of ethylenediaminetetraacetate, etc.

In compositions intended for cleaning silicone rubber contact lenses, quaternary germicides are preferred, particularly benzalkonium chloride (an alkyl substituted dimethylbenzyl-ammonium chloride in which the alkyl substituents are a mixture of $C_8$ to $C_{18}$ alkyl radicals). This compound has minimal potential for toxicity and irritation at the germicidally effective strengths incorporated in the present compositions, and it does not present a signifcant problem of percutaneous absorption by silicone lenses.

In order to maintain sterility of the compositions of the present invention during use, the preferred quaternary or organic mercurial (such as thimerosal sodium) germicide should be present in an amount of about 0.001% to about 0.03% of the overall composition. Preferably, such germicides are present in concentrations of from about 0.004% to about 0.02%, e.g., about 0.01%.

A particularly preferred germicidal ingredient for the cleaning compositions of the present invention is sorbic acid. As previously noted, hydrated gel and cellulose acetate butyrate type lenses complex and concentrate certain common preservatives. Sorbic acid, such as sorbic acid NF XII, has a bacteriacidal effect and is not concentrated by hydrophilic gel, cellulose acetate butyrate or silicone lenses. Thus, sorbic acid is not only an ideal germicidal agent for use with hydrophilic gel lenses, it may be used as a germicide in compositions intended for cleaning any type of lenses. Sorbic acid may be incorporated into the cleaning compositions in amounts between about 0.01% and about 0.5% of the overall composition, and preferably in amounts of about 0.1% to about 0.25%.

The germicidal agents of the compositions of the present invention may also comprise a salt of ethylenediaminetetraacetic acid, such as disodium or trisodium ethylenediaminetetraacetate. Salts of ethylenediaminetetraacetic acid, which serve as combination germicides and chelating agents, are particularly effective when used in combination with other germicides. These salts are not concentrated by silicone, cellulose acetate butyrate, or hydrophilic gel lenses.

A particularly effective germicide, in compositions intended for cleaning silicone contact lenses, is the combination of a quaternary germicide and about 0.01% to about 2% of a salt of ethylenediaminetetraacetic acid, preferably trisodium ethylenediaminetetraacetate. The inclusion of a salt of ethylenediaminetetraacetic acid, particularly the trisodium salt, maintains the pH of the composition at alkaline levels, i.e., above a pH of 7, and preferably at a pH of from 8 to 9. The alkalinity of the solution enhances the germicidal activity of quaternary germicides, such as benzalkonium chloride, and also enhances the solvent activity of the composition for proteins, fats, and mucopolysaccharides that accumulate on the plastic surfaces of contact lenses from contact with body tissues and fluids during normal use.

Specifically, trisodium ethylenediaminetetraacetate enhances the germicidal action of benzalkonium chloride against certain gram negative organisms including *Pseudomonas aeruginosa, Alcaligenese faecalis,* and *Escherichia coli.* The enhancement of germicidal activity is particularly significant in the alkaline environment.

The alkalinity of the compositions of this invention produced by the use of trisodium ethylenediaminetetraacetate also improves the chelating ability and therefore the water softening characteristics of the trisodium ethylenediaminetetraacetate, a property that is desirable in a cleaning and germicidal composition for contact lenses. These chelating and water softening properties of the solution are important because divalent and trivalent cations often present in ocular fluids can reduce the germicidal potency of benzalkonium chloride by blocking the surfaces of the lenses to be cleaned.

Disodium ethylenediaminetetraacetate (sodium edetate) also provides additional protection against pseudomonal contamination, and also acts as a chelating or water softening agent. The sodium edetate ties up divalent and trivalent cations often present in the water, thereby preventing undesirable precipitates from forming the ultimately fogging the contact lens surface. Other salts of ethylenediaminetetraacetate, such as the dipotassium salt can be used.

Another particularly preferred germicide for use with the present invention comprises the combination of sorbic acid with from about 0.01% to about 1% of a salt of ethylenediaminetetraacetic acid. Sorbic acid in the cleaning composition has greater effectiveness at lower pH values. Accordingly, sorbic acid containing cleaning compositions are desirably maintained at a pH of 7 or below, e.g., at a pH of about 6. Preferably, disodium ethylenediaminetetraacetate is used in combination with sorbic acid because trisodium ethylenediaminetetraacetate maintains the composition at a higher pH range.

Disodium ethylenediaminetetraacetate has a bacteria static effect by itself, and in combination with sorbic acid provides a cleaning solution having good bacteriacidal properties. In a composition suitable for cleaning conventional polymethacrylate hard lenses, flexible polyhydroxylated hydrophilic gel lenses, flexible silicone lenses, or cellulose acetated butyrate lenses, a very suitable germicidal composition comprises from about 0.01% to about 0.5%, e.g., 0.25%, sorbic acid in combination with from about 0.01% to about 1%, e.g., 0.5%, disodium ethylenediaminetetraacetate.

The aqueous contact lens cleaning compositions of the present invention include about 2% to about 25%, and preferably about 5% to about 20%, ethyl or isopropyl alcohol. The inclusion of ethyl or isopropyl alcohol is important with respect to insuring removal of cholesterol like material from the lenses.

To insure removal of cholesterol like material from the contact lenses, the compositions of the present invention should also include from about 2% to about 25%, preferably from about 5% to about 15%, of an imidazole amphoteric surfactant having the following formula:

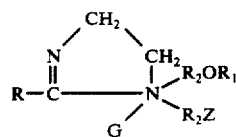

in which R is a $C_6$ to $C_{24}$ hydrocarbon radical, such as a straight or branch chain, saturated or unsaturated, aliphatic hydrocarbon or an alkyl-aryl group in which the alkyl group contains at least six carbon atoms, and preferably a fatty acid radical; $R_1$ is H, alkali metal, preferably Na, or $CH_2COOM$; the $R_2$ groups, which may be the same or different are $C_1$ to $C_4$ alkylene groups, such as $-CH_2-$, $-C_2H_4-$, $-C_3H_6-$ or $-C_4H_8-$; Z is

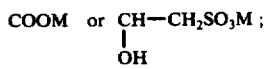

M is alkali metal, preferably Na, H, or a nitrogen containing organic base radical; and G is OH, the salt of a $C_6$ to $C_{24}$ anionic surface active sulfate or sulfonate, such as a saturated or unsaturated aliphatic sulfate or sulfonate, or an alkyl-aryl sulfate or sulfonate in which the alkyl group contains at least 6 carbon atoms, or an acid salt. Such amphoteric surfactants are available from the Miranol Chemical Company, Inc., under the tradename Miranol Amphoteric Surface Active Agents.

Particularly preferred amphoteric surfactants corresponding to the above formula are the dicarboxylates, i.e., Z is COOM and $R_1$ is $CH_2COOM$. Specific examples of preferred fatty acid radical forming substituents (R) are coconut oil, lauric acid, capric acid, caprylic acid, ethylhexoic acid, oleic acid, linoleic acid, stearic acid, and mixtures thereof.

Suitable nitrogen organic base radicals include ammonium, amines, or alcohol or alkylol amines such as, for exanple, mono-di, and triethanolamine and mixtures thereof, propanolamines, butanolamines, polynitrogenous amines such as ethylene diamine, ethylene triamine and the like, pyridine, methylpyridine, piperidine, quaternary ammonium bases such as tetraethyl ammonium hydroxide, tetra-methyl ammonium hydroxide, and in general, primary, secondary and tertiary amines substituted or not with other radicals such as hydroxy, alkyl, aryl, cycloalkyl groups, and the like.

An amphoteric surfactants, available as Miranol $H_2M$ concentrate, of the following formula is particularly preferred:

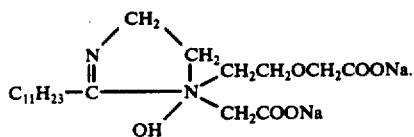

Other specific examples of suitable amphoteric surfactants, and methods of making them can be found in U.S. Pat. Nos. 2,781,349; 2,781,350; 2,781,351; 3,231,580; 3,231,581; 3,452,042; 3,658,985; and 3,697,452.

Amphoteric surfactants of the type described above do not tend to form insoluble internal salts, are non-toxic, and are completely non-irritating to skin and eyes. These surfactants also have some germicidal and fungicidal properties, as well as excellent detergency and wetting properties.

While not essential, since the compositions of the present invention are not intended for direct insertion into the eye, the cleaning compositions may include at least one essentially neutral water-soluble compatible salt to provide tonicity compatible with human tear fluid. Specifically, the compositions may include a sufficient amount of at least one water-soluble salt compatible with ocular tissue to provide a solution salt content equivalent to about 0.5% to about 1.8% sodium chloride.

Preferably, the tonicity of the solutions is isotonic whith human serum and tear fluid, e.g., the compositions are formulated to contain the same salt concentration as that present in the serum and tear fluid of the user. The normal tonicity of human serum and tear fluid is 0.9% (9.0 grams of sodium chloride per liter of fluid), and normally, isotonic solutions contain approximately 0.9% sodium chloride or other salts or mixtures of salts having a tonicity approximately equivalent to that of a 0.9% sodium chloride solution. The tonicity of the solution, however, can be as low as 0.5% or as high as 1.8%.

Any soluble salt or mixtures of salts compatible with ocular tissue can be used to provide the desired tonicity. Preferably, sodium chloride, potassium chloride, or mixtures thereof, are used to provide the desired tonicity. It is understood, however, that one or more essentially neutral, water-soluble alkali or alkaline earth metal salts can be substituted in whole or in part for the sodium or potassium chloride in the solutions of the invention, when tonicity adjustment is desired.

Specific examples of other salts which may be employed include sodium bromide, sodium borate, potassium flouride, potassium bromide, sodium sulfate, potassium sulfate, sodium nitrate, sodium phosphate, potassium nitrate, or potassium phosphate. The tonicity of the cleaning compositions are stated in terms of the sodium chloride, and when other salts are used, they should be present in amounts equivalent to the tonicity of about 0.5% to about 1.8% sodium chloride solutions. It is particularly preferred to adjust the tonicity with a mixture of sodium and potassium chloride in amounts of, respectively, about 0.65% and about 0.20%.

The cleaning compositions of the present invention comprise aqueous solutions. The inert nature of water, and the fact that it is a good solvent for the other ingredients of the present invention, together with its ready availability, make it a desirable base material for the compositions of the present invention. The water used in the solution is preferably purified by distillation, filtration, ion-exchange, or the like. The cleaning compositions of the present invention may vary in consistency from solutions of fairly low viscosity to gels.

In a typical regimen for cleaning contact lenses, regardless of type, the wearer would clean the lenses with the compositions of the present invention immediately after they are removed from the eye, followed by water or isotonic salt solution rinsing of the lenses. The lenses could then be subjected to normal treatment for preserving their sterility. For example, in the case of hydrophilic gel lenses, after cleaning the lenses could be subjected to boiling in normal saline and stored hermetically in the saline solution until ready for use. The boiling fluid should, of course, contain a protective preservative to provide chemical resterilizing capacity in the event the seal in the boiling container fails. The presence of a preservative should also be helpful if the container is open to expose the lenses to non-sterile air for any significant period of time prior to wearing the lenses.

The cleaning compositions of the present invention markedly improves the cleanliness and preserves the optical clarity of lenses, particularly soft lenses. Furthermore, discomfort and eye irritation associated with wearing contact lenses is markedly decreased when a cleaning step with the composition of the present invention is incorporated into the daily care regimen of all types of contact lens wearers.

All parts and percentages referred to in this specification and the appended claims are by weight in terms of unit volume of the solution, unless otherwise specifically indicated. Thus, a sorbic acid content of 0.1% in the solution is equivalent to 1 gram of sorbic acid per liter of solution.

For a clearer understanding of the invention, specific examples of it are set forth below. These examples, which include preferred embodiments, are merely illustrative and are not to be understood as limiting the scope and underlying principles of the invention in any way.

EXAMPLE 1

A cleaning composition containing the following ingredients was prepared:

| | |
|---|---|
| Polyoxyethylene-polyoxypropylene condensate (Pluronic F-127) | 18% |
| Sorbic Acid NF XIII | 0.25% |
| Disodium ethylenediaminetetraacetate | 0.25% |
| Sodium chloride | 0.65% |
| Potassium chloride | 0.20% |
| Deionized water Q.S. | 100% |

This composition was used to clean very dirty silicone lenses, cellulose acetate butyrate lenses, and hydrophilic gel lenses made from hydroxyethylmethacrylate copolymerized with polyvinylpyrrolidone and various other agents. By visual inspection, the three types of lenses appear to be substantially cleaner after treatment with the composition.

Both prior to and after cleaning, a drop of distilled water was placed on the lenses and the contact angle was estimated by casting an enlarged shadow on a screen. The contact angle is the angle a drop of liquid makes with a supporting surface, and is thus a measure of wettability and cleanness of the surface.

The contact angle of the silicone lens, prior to cleaning, was 90°. Subsequent to cleaning, the contact angle had been reduced to 70°. The contact angle of the dirty hydrophilic gel lens was reduced from 70° to 20° after cleaning, while cleaning the dirty cellulose acetate butyrate lens resulted in a reduction of the contact angle from 80° to 20°.

EXAMPLE 2

A cleaning composition in accordance with the present invention was prepared having the following ingredients:

| | |
|---|---|
| Polyoxyethylene-polyoxypropylene condensate (Pluronic F-127) | 15% |
| Sorbic Acid N.F. III | 0.1% |
| Disodium ethylenediaminetetraacetate | 0.5% |
| Isopropyl alcohol | 10% |
| Miranol H2M Concentrate | 10% |
| Deionized water Q.S. | 100% |

The silicone lens treated in Example 1 was cleaned with the above composition. The contact angle was decreased from 50°, prior to cleaning, to 15° after cleaning. The contact angle of the hydrophilic gel lens of Example 1 was reduced to 0° after cleaning with the above composition. The cellulose acetate butyrate lens treated in Example 1 was cleaned with the composition of this Example and the contact angle was reduced to 10°.

The above composition is also very effective for cleaning conventional hard polymethacrylate lenses. The cleaning composition set forth above, unlike the composition of Example 1, is very effective in removing cholesterol like materials found on or in the lenses which have been worn.

Similar cleaning results can be obtained with the composition of this Example when the isopropyl alcohol is replaced with a like amount of ethyl alcohol.

The invention in its broader aspects is not limited to the specific details shown and described, but departures may be made from such details within the scope of the accompanying claims without departing from the principles of the invention and without sacrificing its advantages.

What is claimed is:

1. An aqueous composition for cleaning contact lenses which comprises:

a. about 0.01% to about 40% of a poly (oxyethylene)-poly(oxypropylene) block copolymer having a molecular weight between about 1900 and 15,500, a water solubility in excess of about 10 grams per 100 ml, a cloud point in 1% aqueous solution above about 30° C and a Foam Height in excess of 30 mm;

b. about 2% to about 25% ethyl or isopropyl alcohol; and c. about 2% to about 25% of an amphoteric surfactant having the formula

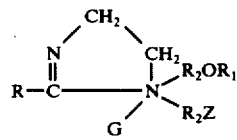

in which R is a $C_6$ to $C_{24}$ hydrocarbon radical, selected from straight or branch chain, saturated or unsaturated, aliphatic hydrocarbon or an alkyl-aryl group in which the alkyl group contains at least six carbon atoms; $R_1$ is H, alkali metal, or $CH_2COOM$; $R_2$ is a $C_1$ to $C_4$ alkylene group; Z is

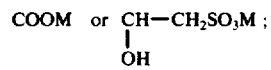

M is alkali metal, H or a nitrogen containing organic base; and G is OH, or a radical comprising the acid group of a $C_6$ to $C_{24}$ anionic surface active sulfate or sulfonate.

2. The composition of claim 1 which contains a germicidal composition, in addition to said alcohol, which germicidal composition is compatible with the lenses and present in a sufficient amount to ensure preservation of the sterility of said aqueous composition.

3. The composition of claim 2 in which the germicidal composition is selected from the group consisting of benzalkorium chloride, thimerosal sodim, sorbic acid, a salt of ethylenediaminetetraacetic acid, and mixtures thereof.

4. The composition of claim 2 wherein the germicidal composition comprises a mixture of sorbic acid and disodium ethylenediaminetetraacetate.

5. The composition of claim 4 wherein the concentration of sorbic acid is from about 0.01% to about 0.5% and the concentration of disodium ethylenediaminetetraacetate is from about 0.01% to about 1%.

6. The composition of claim 4 wherein the concentration of sorbic acid is about 0.25% and the concentration of disodium ethylenediaminetetraacetate is about 0.5%.

7. The composition of claim 1 which contains about 10% to about 25% of said poly(oxyethylene)-poly(oxypropylene) block copolymer.

8. The composition of claim 7 which contains about 15% of said poly(oxyethylene)-poly(oxypropylene) block copolymer.

9. The composition of claim 1 which contains about 5% to about 20% ethyl or isopropyl alcohol.

10. The composition of claim 1 which contains about 5% to about 15% of said amphoteric surfactant.

11. The composition of claim 10 in which said amphoteric surfactant has the formula

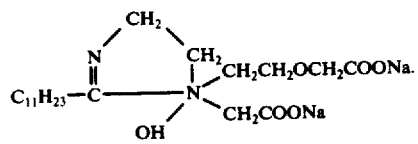

12. The composition of claim 1 which additionally contains a sufficient amount of at least one water-soluble salt compatible with ocular tissue to provide a solution salt content equivalent to about 0.5% to about 1.8% sodium chloride.

13. The composition of claim 12 wherein the water-soluble salt is a mixture of sodium chloride and potassium chloride.

14. The composition of claim 11 wherein the concentration of sodium chloride is about 0.65% and the concentration of potassium chloride is about 0.20%.

15. An aqueous composition for cleaning contact lenses which comprises:
 a. about 10% to about 25% of a poly(oxyethylene)-poly(oxypropylene) block copolymer having a molecular weight between about 1900 and 15,500, a water solubility in excess of about 10 grams per 100 ml, a cloud point in 1% aqueous solution above about 30° C and a Foam Height in excess of 30 mm;
 b. about 5% to about 20% ethyl or isopropyl alcohol; and
 c. about 5% to about 15% of an amphoteric surfactant having the formula

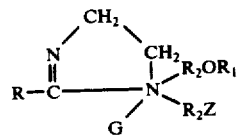

in which R is a $C_6$ to $C_{24}$ hydrocarbon radical, selected from straight or branch chain, saturated or unsaturated, aliphatic hydrocarbon or an alkyl-aryl group in which the alkyl group contains at least six carbon atoms; $R_1$ is H, alkali metal, or $CH_2COOM$; $R_2$ is a $C_1$ to $C_4$ alkylene group; Z is

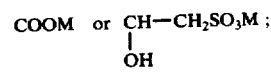

M is alkali metal, H or a nitrogen containing organic base; and G is OH, or a radical comprising the acid group of a $C_6$ to $C_{24}$ anionic surface active sulfate or sulfonate.

16. The composition of claim 15 which contains a germicidal composition, in addition to said alcohol, which germicidal composition is compatible with lenses and present in a sufficient amount to ensure preservation of the sterility of said aqueous composition.

17. The composition of claim 16 wherein the germicidal composition comprises from about 0.01% to about 0.5% sorbic acid and from about 0.01% to about 1% disodium ethylenediaminetetraacetate.

18. The composition of claim 17 wherein in the amphoteric sufactant, R is a fatty acid radical and G is OH.

19. The composition of claim 18 in which said amphoteric surfactant has the formula

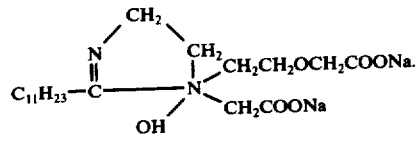

* * * * *